US006251414B1

(12) United States Patent
Lauton et al.

(10) Patent No.: US 6,251,414 B1

(45) Date of Patent: Jun. 26, 2001

(54) AQUEOUS FORMULATION FOR PRETANNING RAW HIDES

(75) Inventors: Alain Lauton, Saint-Louis (FR); Markus Hess, Steinen-Hofen; Günter Streicher, Weil am Rhein, both of (DE); Alois Püntener, Rheinfelden (CH)

(73) Assignee: TFL Ledertechnik GmbH & Co. KG, Weil am Rhein (DE)

( * ) Notice: Subject to any disclaimer, the term of this patent is extended or adjusted under 35 U.S.C. 154(b) by 0 days.

(21) Appl. No.: 09/183,481

(22) Filed: Oct. 30, 1998

Related U.S. Application Data

(62) Division of application No. 08/007,423, filed on Jan. 22, 1993, now abandoned.

(30) Foreign Application Priority Data

Jan. 28, 1992 (CH) ..................... 240/92
Oct. 21, 1992 (CH) ..................... 3261/92

(51) Int. Cl.[7] ..................... A61K 9/00; C14C 1/00; C14C 3/00; C14C 3/08; C14C 3/10; C14C 3/24; C14C 9/00

(52) U.S. Cl. ..................... 424/402; 8/94.15; 8/94.18; 8/94.31; 8/94.32; 8/94.33; 252/8.57; 424/76.1; 424/76.2; 424/76.21

(58) Field of Search ..................... 424/402, 76.1, 424/76.2, 76.21; 252/8.57; 8/94.15, 94.18, 94.31, 94.33, 94.32

(56) References Cited

U.S. PATENT DOCUMENTS

| | | | |
|---|---|---|---|
| 30,393 | 10/1860 | Dietz | 8/94.21 |
| 2,941,859 | 6/1960 | Fein et al. | 8/94.33 |
| 3,909,193 | 9/1975 | Erdmann et al. | 8/94.33 |
| 4,260,228 | 4/1981 | Miyata | 351/160 H |
| 5,011,499 | 4/1991 | Rathfelder et al. | 8/94.33 |
| 5,158,778 | 10/1992 | Donovan et al. | 424/488 |

FOREIGN PATENT DOCUMENTS

| | | |
|---|---|---|
| 190702 | 12/1904 | (DE) . |
| 3001301 | 7/1981 | (DE) . |
| 3308087 | 9/1984 | (DE) . |
| 3811267 | 5/1989 | (DE) . |

OTHER PUBLICATIONS

K. Lassen, Lede–Häutemarkt, 36, 14, pp. 39–42, (1984).

Abstract for DE 3308087.

Derwent Abstr. 82–62845E.

The New Encyclopedia Britannica, vol. 6, p. 35, (1986).

Webster's Third New International Dictionary of the Engish language unabridged, p. 1438.

*Primary Examiner*—Shelley A. Dodson
(74) *Attorney, Agent, or Firm*—Oblon, Spivak, McClelland, Maier & Neustadt, P.C.

(57) ABSTRACT

There is disclosed an aqueous formulation for pretanning leather, which formulation comprises
(a) a reductive saccharide having a dextrose equivalent of 10 to 100, and
(b) an aliphatic dialdehyde containing 2 to 8 carbon atoms, and which is devoid of mineral salts.

The leather treated with the novel aqueous composition (wet white leather) is eminently suitable for further processing, especially for the manufacture of leathers which are devoid of heavy metals.

7 Claims, No Drawings

AQUEOUS FORMULATION FOR PRETANNING RAW HIDES

This application is a divisional of prior application Ser. No. 08/007,423 abandoned filed date Jan. 22, 1993.

The present invention relates to a an aqueous formulation for pretanning raw hides, to a process for pretanning raw hides and to the leather pretanned by the instant process.

Mineral and, in particular, chrome tanning and pretanning is of great importance for the manufacture of leather and hides. However, the chromium salt containing treatment baths resulting from pretanning and the actual tanning process constitute a significant pollution factor for the wastewaters. These ecological considerations have led to a search being made in this art for alternative processes that, on the one hand, are ecologically more acceptable and, on the other, match mineral tanning with regard to the quality of the leather obtained.

Surprisingly, it has now been found that a combination product comprising a reductive saccharide having a dextrose equivalent of 10 to 100 and an aliphatic dialdehyde containing 2 to 8 carbon atoms is a pretanning formulation which makes it possible to carry out a subsequent tanning without mineral, especially chromium, salts for the manufacture of wet white leather material. The novel aqueous formulation at the same time also permits good results to be achieved with regard to pretanning, the leather having a high shrinkage temperature.

Accordingly, the invention provides an aqueous formulation for pretanning leather, which formulation comprises (a) a reductive saccharide having a dextrose equivalent of 10 to 100, and (b) an aliphatic dialdehyde containing 2 to 8 carbon atoms, and is devoid of mineral salts.

Reductive saccharides having a dextrose equivalent of 10 to 100 are the customary aldoses and ketoses, preferably mono- and disaccharides, and also oligosaccharides and polysaccharides.

By dextrose equivalent is meant the amount, calculated in grams, of saccharide that corresponds to 100 grams of dextrose with respect to the reductive capacity.

The novel formulations preferably contain mono- or disaccharides. Suitable monosaccharides are typically glucose, fructose, mannose, arabinose and ribose. Typical representatives of the disaccharides are saccharose, maltose or lactose. It is preferred to use monosaccharides in the process of the invention. Preferred monosaccharides are aldoses, glucose being especially preferred on account of the ease with which it can be obtained and of its availability in technical amounts. Glucose syrups having a dextrose equivalent of 20 to 90, preferably of 40 to 80, are particularly suitable on account of their reasonable price.

The dialdehydes which may suitably be used in the practice of this invention are quite generally all dialdehydes or mixtures thereof that contain 2 to 8 carbon atoms and have structurally saturated aliphatic C—C bonds. Illustrative examples of such dialdehydes are glyoxal, malonaldehyde, succinaldehyde, glutaraldehyde, adipaldehyde, pimelaldehyde as well as the dialdehyde derived from suberic acid. Preferred representatives are succinaldehyde, glutaraldehyde, adipaldehyde and glyoxal, among which glutaraldehyde is especially preferred. The dialdehydes are normally available as commercial dialdehydes which contain 25 to 50% by weight of water.

Preferred aqueous formulations comprise (a) a reductive saccharide having a dextrose equivalent of 10 to 100, and (b) glutaraldehyde.

Particularly interesting aqueous formulations are those comprising (a) a monosaccharide having a dextrose equivalent of 100, and (b) glutaraldehyde.

Further preferred formulations are those comprising (a) a disaccharide having a dextrose equivalent of 20 to 60, and (b) glutaraldehyde.

Particularly preferred aqueous formulations are those comprising (a) glucose and (b) glutaraldehyde.

Preferred novel aqueous formulations comprise, based on the entire formulation 2 to 60% by weight, preferably 10 to 40% by weight, of component (a), 2 to 75% by weight, preferably 30 to 55% by weight, of component (b), and water to make up 100%.

Those aqueous formulations are also preferred which contain, per mol of component (b), 0.05 to 0.19 mol of component (a).

The aqueous formulations are conveniently prepared by dissolving component (a) in water in the temperature range from 15 to 60° C. and subsequently adding component (b) to the resultant clear solution.

The aqueous formulation so obtained is liquid and has good shelf stability. If desired, however, it can also be dried.

The novel aqueous formulation is by itself eminently suitable for use as an excellent pretanning agent for all hides and pelts and is used most particularly as precursor for the manufacture of wet white leathers and pelts.

The invention therefore also relates to a process for pretanning raw hides. The process consists in treating a pickled raw hide in an aqueous liquor comprising (a) a reductive saccharide having a dextrose equivalent of 10 to 100, and (b) an aliphatic dialdehyde containing 2 to 8 carbon atoms, and which is devoid of mineral salts.

It is preferred to use for the process of the invention an aqueous liquor comprising (a) a monosaccharide having a dextrose equivalent of 100, and (b) glutaraldehyde, or (a) a disaccharide having a dextrose equivalent of 40 to 80, and (b) glutaraldehyde.

A particularly preferred embodiment of the inventive process comprises the use of an aqueous liquor comprising (a) glucose and (b) glutaraldehyde.

It is not necessary to add further ingredients to the treatment bath.

The pretanning is typically carried out by treating the pickled hide material with the novel aqueous formulation and subsequently tanning the material so obtained with a mineral tanning agent in conventional manner or, preferably, for the manufacture of wet white material, with vegetable or synthetic tanning agents.

The process of this invention makes it possible to dispense completely with the use of mineral salts.

Finished tanned leathers can also be obtained by carrying out the inventive process in appropriate manner.

In the following Working and Application Examples, parts and percentages are by weight.

EXAMPLE 1

Preparation of the Novel Aqueous Formulation 167 ml of water are charged to a sulfonating flask and heated to 60° C. With good stirring, 167 g of glucose monohydrate (dextrose equivalent 100) are added over 20 minutes. When all has dissolved, 666 g of 50% glutaraldehyde are run in. The resultant clear, pale solution has a pH of 3.9–4.2. The solids content is 50%.

EXAMPLE 2

Application Example 100 parts of a pickled calf hide are treated for 8 to 16 hours at 25° C. in a rotating drum with 1.5% of the formulation prepared according to Example 1. The pH is adjusted to 4.0 with pulverised sodium hydrogen carbonate or sodium form ate.

The leather so obtained (wet white leather) is hydroextracted and shaved to the desired thickness. This pretanned leather is admirably suitable for further processing with mineral, vegetable or synthetic tanning agents to give leathers free from heavy metals.

EXAMPLE 3

117 ml of water are charged to a sulfonating flask. With good stirring, 117 g of glucose monohydrate (dextrose equivalent 100) are added over 20 minutes. When all has dissolved, 666 g of 50% glutaraldehyde are run in at 20° C. The resultant clear, pale solution has a pH of 3.9–4.2. The solids content is 50%.

EXAMPLE 4

666 g of 50% glutaraldehyde are charged to a sulfonating flask. With good stirring, 334g of 50% glucose syrup (average molecular weight 550, dextrose equivalent 60) are run in at room temperature. The resultant clear, pale solution has a pH of 3.9–4.2. The solids content is 50%.

What is claimed is:

1. A process for the manufacture of a leather comprising (1) pre-tanning a raw hide, and (2) tanning the product of (1) with a tanning agent selected from the group consisting of mineral, vegetable and synthetic tanning agents, wherein in (1) a pickled raw hide is treated in an aqueous liquor which is devoid of mineral salts and which comprises (a) a reductive saccharide having a dextrose equivalent of 10 to 100, and (b) an aliphatic dialdehyde containing 2 to 8 carbon atoms.

2. A process according to claim 1, wherein the aqueous liquor used for pretanning comprises (a) a monosaccharide having a dextrose equivalent of 100 and (b) glutaraldehyde, or (a) a disaccharide having a dextrose equivalent of 40 to 80, and (b) glutaraldehyde.

3. A process according to claim 2, wherein the aqueous liquor used for pretanning comprises (a) glucose and (b) glutaraldehyde.

4. A process according to claim 1, wherein the aqueous liquor for pretanning comprises per mol of component (b) 0.05 to 0.19 mol of component (a).

5. The method as claimed in claim 1, wherein in 2 the product is tanned with a mineral tanning agent.

6. The process as claimed in claim 1, wherein in 2 the product is tanned with a vegetable tanning agent.

7. The process as claimed in claim 1, wherein in 2 the product is tanned with a synthetic tanning agent.

* * * * *

UNITED STATES PATENT AND TRADEMARK OFFICE
CERTIFICATE OF CORRECTION

PATENT NO. : 6,251,414 B1
DATED : June 26, 2001
INVENTOR(S) : Alain Lauton et al.

It is certified that error appears in the above-identified patent and that said Letters Patent is hereby corrected as shown below:

Column 1,
Line 6, delete "a".

Column 2,
Line 28, "C." should read -- C --.

Column 3,
Line 16, "25° C." should read -- 25° C --.
Line 19, "form ate" should read -- formate --.

Signed and Sealed this

Second Day of April, 2002

*Attest:*

JAMES E. ROGAN

*Attesting Officer*

*Director of the United States Patent and Trademark Office*